United States Patent
Richard et al.

(10) Patent No.: US 7,727,541 B2
(45) Date of Patent: Jun. 1, 2010

(54) MEDICAL DEVICES HAVING POLYMERIC REGIONS BASED ON VINYL ETHER BLOCK COPOLYMERS

(75) Inventors: Robert E. Richard, Wrentham, MA (US); Marlene C. Schwarz, Auburndale, MA (US); Mark Boden, Harrisville, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 721 days.

(21) Appl. No.: 11/436,813

(22) Filed: May 18, 2006

(65) Prior Publication Data

US 2007/0269485 A1 Nov. 22, 2007

(51) Int. Cl.
*A61F 2/86* (2006.01)
*A61F 2/82* (2006.01)
*A61K 47/32* (2006.01)

(52) U.S. Cl. .................................. 424/423; 514/772.4
(58) Field of Classification Search ........................ None
See application file for complete search history.

(56) References Cited

U.S. PATENT DOCUMENTS

| 5,733,925 | A | 3/1998 | Kunz et al. |
| 6,545,097 | B2 | 4/2003 | Pinchuk et al. |
| 2002/0107330 | A1 | 8/2002 | Pinchuk et al. |
| 2002/0193336 | A1* | 12/2002 | Elkins et al. ................... 514/44 |
| 2003/0236514 | A1 | 12/2003 | Schwarz |
| 2005/0025803 | A1 | 2/2005 | Richard et al. |
| 2005/0064011 | A1 | 3/2005 | Song et al. |
| 2005/0112172 | A1 | 5/2005 | Pacetti |
| 2006/0013849 | A1 | 1/2006 | Strickler et al. |
| 2006/0013853 | A1 | 1/2006 | Richard |
| 2006/0013854 | A1 | 1/2006 | Strickler et al. |

OTHER PUBLICATIONS

Reyntjens et al. (Polymers for Advanced Technologies 2001, 12, 107-122).*
Shamakhmudova et al. (Russian Chemical Bulletin 1964, 13(4), 656-661).*

* cited by examiner

*Primary Examiner*—Ernst V Arnold
(74) *Attorney, Agent, or Firm*—Mayer & Williams PC; David B. Bonham; Keum J. Park

(57) ABSTRACT

According to an aspect of the present invention, implantable or insertable medical devices are provided, which contain one or more polymeric regions, which in turn contain at least one block copolymer. The block copolymer includes (a) at least one high $T_g$ (glass transition temperature) polymer block that contains at least one high $T_g$ vinyl ether monomer and (b) at least one low $T_g$ polymer block that contains at least one low $T_g$ vinyl ether monomer.

27 Claims, 3 Drawing Sheets

MEDICAL DEVICES HAVING POLYMERIC REGIONS BASED ON VINYL ETHER BLOCK COPOLYMERS

FIELD OF THE INVENTION

The present invention relates generally to medical devices, and more particularly to implantable or insertable medical devices which contain polymeric regions.

BACKGROUND OF THE INVENTION

Controlled release of therapeutic agents by means of polymeric materials has existed in various forms for many years. For example, many state-of-the-art medical devices for therapeutic agent delivery have a biostable or biodegradable polymeric coating, which serves as the reservoir for one or more therapeutic agents. Methods of changing the release rate of the therapeutic agent from the coating include changing the therapeutic loading, adding additional polymers to change the hydrophilic/hydrophobic balance of the coating, the use of polymeric barrier layers, and changing the degradation rate (for biodegradable materials). Examples of such medical devices include drug eluting coronary stents commercially available from Boston Scientific (TAXUS), Johnson & Johnson (CYPHER) and others.

Many types of polymeric materials have been used in medical devices. Examples include block copolymers based on poly(butyl methacrylate), poly(vinyl acetate) and polyisobutylene (PIB). It has been found that block copolymers based on PIB have excellent biocompatibility and mechanical properties that make them extremely well suited for use in medical device devices. For instance, block copolymers based on PIB, such as poly(styrene-b-isobutylene-b-styrene), which are typically prepared by living cationic polymerization, have been found to have desirable properties for medical device coatings, particularly those intended to deliver therapeutic agents to the vasculature. These include strength, elasticity, coating conformability, vascular compatibility and biostability, among others.

SUMMARY OF THE INVENTION

According to an aspect of the present invention, implantable or insertable medical devices are provided, which contain one or more polymeric regions, which in turn contain at least one block copolymer. The block copolymer includes (a) at least one high $T_g$ (glass transition temperature) polymer block that contains at least one high $T_g$ vinyl ether monomer and (b) at least one low $T_g$ polymer block that contains at least one low $T_g$ vinyl ether monomer.

Advantages of the present invention include one or more of the following:

Polymeric regions can be formed which have therapeutic release profiles which can be varied with composition.

Polymeric regions can be formed which have good coating conformability.

These and other aspects, embodiments and advantages of the present invention will become immediately apparent to those of ordinary skill in the art upon review of the Detailed Description and Claims to follow.

DETAILED DESCRIPTION OF THE INVENTION

Figure 1:
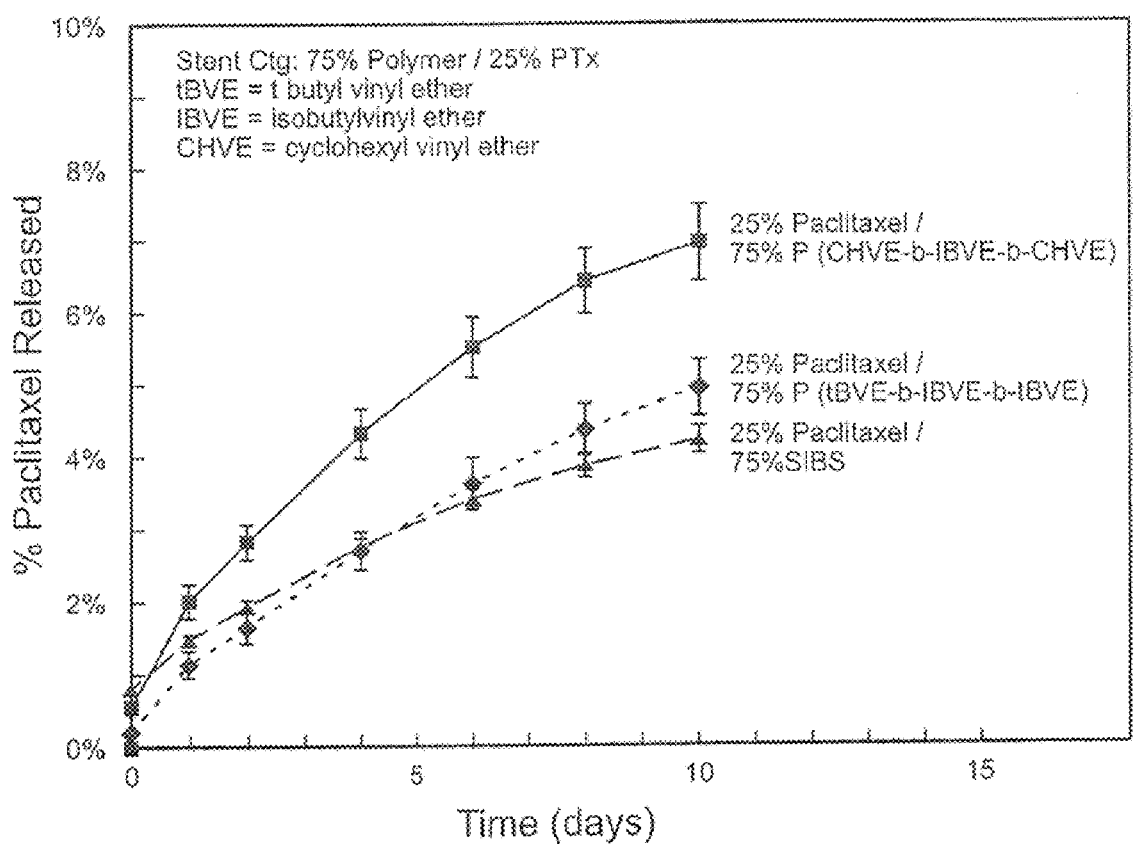
FIG. 1 is a graphical depiction of paclitaxel release as a function of time in PBS containing 0.5 wt % Tween® 20 (polyoxyethylene(20) sorbitan monolaurate) for polymer coatings containing paclitaxel and one of the following polymers: (a) poly(cyclohexyl vinyl ether-b-isobutyl vinyl ether-b-cyclohexyl vinyl ether), in accordance with an embodiment of the invention, (b) poly(t-butyl vinyl ether-b-isobutyl vinyl ether-b-t-butyl vinyl ether), in accordance with an embodiment of the invention, and (c) poly(styrene-b-isobutylene-b-styrene triblock copolymer (SIBS).

As noted above, in one aspect, the present invention provides implantable or insertable medical devices, which contain one or more polymeric regions, which in turn contain at least one block copolymer. The block copolymer includes (a) at least one high $T_g$ (glass transition temperature) polymer block that contains at least one high $T_g$ vinyl ether monomer and (b) at least one low $T_g$ polymer block that contains at least one low $T_g$ vinyl ether monomer.

As used herein a "polymeric region" is a region that contains one or more types of polymers, and typically contains at least 50 wt % polymers, at least 75 wt % polymers, or even more.

As used herein, "polymers" are molecules containing multiple copies (e.g., 5 to 10 to 25 to 50 to 100 to 250 to 500 to 1000 or more copies) of one or more constitutional units, commonly referred to as monomers.

Polymers may take on a number of configurations, which may be selected, for example, from cyclic, linear and branched configurations. Branched configurations include star-shaped configurations (e.g., configurations in which three or more chains emanate from a single branch point, such as a seed molecule), comb configurations (e.g., configurations having a main chain and a plurality of side chains), dendritic configurations (e.g., arborescent and hyperbranched polymers), and so forth.

As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block copolymers.

As used herein, "block copolymers" are copolymers that contain two or more differing polymer blocks, for instance, because a constitutional unit (i.e., monomer) is found in one polymer block that is not found in another polymer block. As used herein, a "polymer block" is a grouping of constitutional units (e.g., 5 to 10 to 25 to 50 to 100 to 250 to 500 to 1000 or more units). Blocks can be branched or unbranched. Blocks can contain a single type of constitutional unit (also referred to herein as "homopolymeric blocks") or multiple types of constitutional units (also referred to herein as "copolymeric blocks") which may be provided, for example, in a random, statistical, gradient, or periodic (e.g., alternating) distribution.

A "low $T_g$ polymer block" is a polymer block that displays a glass transition temperature ($T_g$), as measured by any of a number of techniques such as differential scanning calorimetry (DSC), that is below body temperature, typically from 37° C. to 35° C. to 30° C. to 25° C. to 0° C. to −25° C. to −50°

C. or below. "Body temperature" will depend upon the subject being treated and averages 37° C. for humans. As a result of their low glass transition temperatures, low $T_g$ polymer blocks are typically elastomeric at ambient temperature. A "low $T_g$ monomer" is a monomer that, when in homopolymer form, displays a glass transition temperature ($T_g$) that is below body temperature, more typically from 37° C. to 35° C. to 30° C. to 25° C. to 0° C. to −25° C. to −50° C. or below.

Conversely, an elevated or "high $T_g$ polymer block" is a polymer block that displays a glass transition temperature which is above body temperature, typically from 37° C. to 40° C. to 45° C. to 50° C. to 60° C. to 75° C. to 100° C. or above. A "high $T_g$ monomer" is a monomer that, when in homopolymer form, displays a glass transition temperature ($T_g$) that is above body temperature, typically from 37° C. to 40° C. to 45° C. to 50° C. to 60° C. to 75° C. to 100° C. or above.

Examples of such structures include (a) block copolymers having alternating blocks of the type $(HL)_m$, $L(HL)_m$ and $H(LH)_m$ where L is a low $T_g$ polymer block, H is a high $T_g$ polymer block, m is a positive whole number of 1 or more, and (b) block copolymers having multi-arm geometries, such as $X(LH)_n$, and $X(HL)_n$, where n is a positive whole number of 2 or more and X is a hub species (e.g., an initiator molecule residue, a residue of a molecule to which preformed polymer chains are attached, etc.) Note that hub species and other non-polymer-chain species are generally ignored in describing block copolymer morphology. For example, $X(LH)_2$ is generally designated as an HLH triblock copolymer. Examples of other non-polymer-chain species, which are commonly present in copolymers, include capping molecules, and linking residues. Other examples of block copolymers include comb copolymers having an L chain backbone and multiple H side chains, as well as comb copolymers having an H chain backbone and multiple L side chains.

Vinyl ether monomers for the practice of the invention include substituted, protected-substituted and unsubstituted cycloalkyl vinyl ethers, substituted, protected-substituted and unsubstituted linear alkyl vinyl ethers, and substituted, protected-substituted and unsubstituted branched alkyl vinyl ethers, where the alkyl groups contain from 1 to 20 carbon atoms. Specific low $T_g$ vinyl ether monomers include alkyl vinyl ethers such as methyl vinyl ether ($T_g$ −31° C.), ethyl vinyl ether ($T_g$ −43° C.), propyl vinyl ether ($T_g$ −49° C.), butyl vinyl ether ($T_g$ −55° C.), isobutyl vinyl ether ($T_g$ −19° C), 2-ethylhexyl vinyl ether ($T_g$ −66° C.) and dodecyl vinyl ether ($T_g$ −62° C.). Specific high $T_g$ vinyl ether monomers include alkyl vinyl ethers such as tert-butyl vinyl ether ($T_g$ 88° C.) and cyclohexyl vinyl ether ($T_g$ 81° C.). Vinyl ether monomers for the practice of the invention further include aryl vinyl ethers, including substituted aryl vinyl ethers (e.g., chloromethyl or alkyl substituted aryl vinyl ethers), protected substituted aryl vinyl ethers (e.g., protected hydroxyl or amine aryl vinyl ethers), and unsubstituted aryl vinyl ethers (e.g., phenyl vinyl ether), where the aryl group may contain from 6 to 20 carbon atoms.

Block copolymers in accordance with the invention may, or may not, comprise further monomers. For example, the block copolymers may further comprise (or exclude) monomers selected from the following, among others: (a) acrylic acid monomers such as the following: acrylic acid and its salt forms (e.g., potassium acrylate and sodium acrylate); acrylic acid anhydride; acrylic acid esters including alkyl acrylates (e.g., methyl acrylate, ethyl acrylate, propyl acrylate, isopropyl acrylate, butyl acrylate, sec-butyl acrylate, isobutyl acrylate, tert-butyl acrylate, hexyl acrylate, cyclohexyl acrylate, isobornyl acrylate, 2-ethylhexyl acrylate, dodecyl acrylate and hexadecyl acrylate), arylalkyl acrylates (e.g., benzyl acrylate), alkoxyalkyl acrylates (e.g., 2-ethoxyethyl acrylate and 2-methoxyethyl acrylate), halo-alkyl acrylates (e.g., 2,2,2-trifluoroethyl acrylate) and cyano-alkyl acrylates (e.g., 2-cyanoethyl acrylate); acrylic acid amides (e.g., acrylamide, N-isopropylacrylamide and N,N dimethylacrylamide); and other acrylic-acid derivatives (e.g., acrylonitrile); (b) methacrylic acid monomers such as the following: methacrylic acid and its salts (e.g., sodium methacrylate); methacrylic acid anhydride; methacrylic acid esters (methacrylates) including alkyl methacrylates (e.g., methyl methacrylate, ethyl methacrylate, isopropyl methacrylate, butyl methacrylate, isobutyl methacrylate, t-butyl methacrylate, hexyl methacrylate, cyclohexyl methacrylate, 2-ethylhexyl methacrylate, octyl methacrylate, dodecyl methacrylate, hexadecyl methacrylate, octadecyl methacrylate, aromatic methacrylates (e.g., phenyl methacrylate and benzyl methacrylate), hydroxyalkyl methacrylates (e.g., 2-hydroxyethyl methacrylate and 2-hydroxypropyl methacrylate), aminoalkyl methacrylates (e.g., diethylaminoethyl methacrylate and 2-tert-butyl-aminoethyl methacrylate), additional methacrylates (e.g., isobornyl methacrylate and trimethylsilyl methacrylate); and other methacrylic-acid derivatives (e.g., methacrylonitrile); (c) vinyl aromatic monomers (i.e., those having aromatic and vinyl moieties) such as the following: unsubstituted vinyl aromatics (e.g., styrene and 2-vinyl naphthalene); vinyl substituted aromatics (e.g., α-methyl styrene); and ring-substituted vinyl aromatics including ring-alkylated vinyl aromatics (e.g., 3-methylstyrene, 4-methylstyrene, 2,4-dimethylstyrene, 2,5-dimethylstyrene, 3,5-dimethylstyrene, 2,4,6-trimethylstyrene, and 4-tert-butylstyrene), ring-alkoxylated vinyl aromatics (e.g., 4-methoxystyrene and 4-ethoxystyrene), ring-halogenated vinyl aromatics (e.g., 2-chlorostyrene, 3-chlorostyrene, 4-chlorostyrene, 2,6-dichlorostyrene, 4-bromostyrene and 4-fluorostyrene) and ring-ester-substituted vinyl aromatics (e.g., 4-acetoxystyrene); (d) vinyl monomers (beyond the above vinyl aromatic monomers) such as the following: vinyl alcohol; vinyl esters (e.g., vinyl benzoate, vinyl 4-tert-butyl benzoate, vinyl cyclohexanoate, vinyl pivalate, vinyl trifluoroacetate and vinyl butyral); vinyl amines (e.g., 2-vinyl pyridine, 4-vinyl pyridine, and vinyl carbazole); vinyl halides (e.g., vinyl chloride and vinyl fluoride); and other vinyl compounds (e.g., 1-vinyl-2-pyrrolidone and vinyl ferrocene); (e) aromatic monomers (beyond the above vinyl aromatic monomers) such as acenaphthalene and indene; (f) cyclic ether monomers such as the following: tetrahydrofuran, trimethylene oxide, methyl glycidyl ether, butyl glycidyl ether, allyl glycidyl ether, epibromohydrin, epichlorohydrin, 1,2-epoxybutane, 1,2-epoxyoctane and 1,2-epoxydecane; (g) ester monomers (beyond those ester monomers listed above) such as ethylene malonate, vinyl acetate and vinyl propionate; (h) alkene monomers such as the following: unsubstituted alkene monomers (e.g., ethylene, propylene, isobutylene, 1-butene, trans-butadiene, 4-methyl pentene, 1-octene, 1-octadecene, and other α-olefins, as well as cis-isoprene and trans-isoprene) and halogenated alkene monomers (e.g., vinylidene chloride, vinylidene fluoride, cis-chlorobutadiene, trans-chlorobutadiene, and tetrafluoroethylene); and (i) organo-siloxane monomers such as dimethylsiloxane, diethylsiloxane, methylethylsiloxane, methylphenylsiloxane and diphenylsiloxane.

Various polymerization techniques may be used to form the above copolymers, including cationic and radical polymerization methods, both living and non-living. Thus, like the polyisobutylene based block copolymers described above, these copolymers may be produced by living cationic polymerization. Like the polyisobutylene-polyalkene based block copolymers described above, for example, poly(styrene-b- isobutylene-b-styrene), these polymers are typically elastomeric block copolymers. In addition, by varying the polarity of such polymers with functional or protected groups such as hydroxyl (e.g., using silyl-protected hydroxyalkyl vinyl ether monomers), one may make polymers with potential tunable therapeutic release. Also, since these polymers have a saturated polymer backbone, and the side groups contain ether groups, these polymers are expected to be biostable. As seen in the Examples below, it has been found that polyvinyl-ether-based block copolymers can be formed, which (a) can be coated onto coronary stents and (b) have paclitaxel release performance that can be varied with composition. The mechanical properties of these coatings were found to be acceptable as well, as seen in the SEM images below, where no cracking or rupturing was observed upon stent expansion.

Medical devices benefiting from the present invention include a variety of implantable or insertable medical devices, which are implanted or inserted into a subject, either for procedural uses or as implants. Examples include catheters (e.g., renal or vascular catheters such as balloon catheters), guide wires, balloons, filters (e.g., vena cava filters), stents (including coronary artery stents, peripheral vascular stents such as cerebral stents, urethral stents, ureteral stents, biliary stents, tracheal stents, gastrointestinal stents and esophageal stents), stent grafts, vascular grafts, vascular access ports, embolization devices including cerebral aneurysm filler coils (including Guglilmi detachable coils and metal coils), microspheres or other particles, myocardial plugs, pacemaker leads, left ventricular assist hearts and pumps, total artificial hearts, heart valves, vascular valves, tissue bulking devices, tissue engineering scaffolds for cartilage, bone, skin and other in vivo tissue regeneration, cochlear implants, sutures, suture anchors, anastomosis clips and rings, tissue staples and ligating clips at surgical sites, cannulae, metal wire ligatures, orthopedic prosthesis such as bone grafts, bone plates, joint prostheses, as well as various other medical devices that are adapted for implantation or insertion into the body.

The medical devices of the present invention include implantable and insertable medical devices that are used for systemic treatment, as well as those that are used for the localized treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, ears, spine, nervous system, lungs, trachea, esophagus, intestines, stomach, brain, liver and pancreas, skeletal muscle, smooth muscle, breast, dermal tissue, cartilage, tooth and bone.

As used herein, "treatment" refers to the prevention of a disease or condition, the reduction or elimination of symptoms associated with a disease or condition, or the substantial or complete elimination of a disease or condition. Preferred subjects (also referred to as "patients") are vertebrate subjects, more preferably mammalian subjects and more preferably human subjects. Specific examples of medical devices for use in conjunction with the present invention include vascular stents, such as coronary stents and cerebral stents, which deliver a therapeutic agent into the vasculature for the treatment of restenosis.

In some embodiments, the polymeric regions of the present invention correspond to an entire medical device. In other embodiments, the polymeric regions correspond or to one or more portions of a medical device. For instance, the polymeric regions can be in the form of one or more medical device components, in the form of one or more fibers which are incorporated into a medical device, in the form of one or more polymeric layers formed over all or only a portion of an underlying medical device substrate, and so forth. Layers can be provided over an underlying substrate at a variety of locations, and in a variety of shapes (e.g., in desired patterns, for instance, using appropriate application or masking techniques), and they can be of different compositions. As used herein a "layer" of a given material is a region of that material whose thickness is small compared to both its length and width. As used herein a layer need not be planar, for example, taking on the contours of an underlying substrate. Layers can be discontinuous (e.g., patterned). Terms such as "film," "layer" and "coating" may be used interchangeably herein.

Materials for use as underlying substrates include polymeric materials, ceramic materials and metallic materials.

Specific examples of ceramic substrate materials may be selected, for example, from materials containing one or more of the following: metal oxides, including aluminum oxides and transition metal oxides (e.g., oxides of titanium, zirconium, hafnium, tantalum, molybdenum, tungsten, rhenium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon and carbon-based, ceramic-like materials such as carbon nitrides, among many others.

Specific examples of metallic substrate materials may be selected, for example, from materials containing one or more of the following: metals (e.g., biostable metals such as gold, platinum, palladium, iridium, osmium, rhodium, titanium, tantalum, tungsten, and ruthenium, and bioresorbable metals such as magnesium) and metal alloys, including metal alloys comprising iron and chromium (e.g., stainless steels, including platinum-enriched radiopaque stainless steel), alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), and alloys comprising nickel and chromium (e.g., inconel alloys).

Specific examples of polymeric substrate materials may be selected, for example, from materials containing one or more of the polymers listed below as supplemental polymers.

In some aspects, the polymeric regions of the present invention control the release of one or more therapeutic agents, in which case the therapeutic agent may be disposed, for example, beneath and/or within the polymeric region. Such "polymeric release regions" include carrier regions and barrier regions. By "carrier region" is meant a polymeric release region which further comprises a therapeutic agent and from which the therapeutic agent is released. For example, in some embodiments, the carrier region constitutes the entirety of the medical device (e.g., provided in the form of a stent body). In other embodiments, the carrier region corresponds to only a portion of the device (e.g., a coating overlying a medical device substrate such as a stent body). By "barrier region" is meant a region which is disposed between a source of therapeutic agent and a site of intended release, and which controls the rate at which therapeutic agent is released. For example, in some embodiments, the medical device consists of a barrier region that surrounds a source of therapeutic agent. In other embodiments, the barrier region is disposed over a source of therapeutic agent, which is in turn disposed over all or a portion of a medical device substrate.

In addition to the attributes of the polymer or polymers making up the polymeric release regions, the therapeutic agent release profile is also affected by other factors such as the size, number and/or position of the polymeric release regions within the device. For example, the release profile of polymeric carrier and barrier layers in accordance with the presenting invention can be modified by varying the thickness and/or surface areas of the same. Moreover, multiple polymeric regions can be employed to modify the release profile. For example, multiple carrier or barrier layers of the invention, either having the same or different content (e.g., different polymeric and/or therapeutic agent content), can be stacked on top of one another (hence, carrier layers can act as barrier layers in some embodiments), can be positioned laterally with respect to one another, and so forth.

As a specific example, for tubular devices such as stents (which can comprise, for example, a laser or mechanically cut tube, one or more braided, woven, or knitted filaments, etc.), polymeric release layers can be provided on the luminal surfaces, on the abluminal surfaces, on the lateral surfaces between the luminal and abluminal surfaces (including the ends), patterned along the luminal or abluminal length of the devices, and so forth. Moreover, release layers can control the release of the same or different therapeutic agents. It is therefore possible, for example, to release the same or different therapeutic agents at different rates from different locations on the medical device. As another specific example, it is possible to provide a tubular medical device (e.g., a vascular stent) having a first release layer which contains or is disposed over a first biologically active agent (e.g., an antithrombotic agent) at its inner, luminal surface and a second release layer which contains or is disposed over a second biologically active agent that differs from the first biologically active agent (e.g., an antiproliferative agent) at its outer, abluminal surface (as well as on the ends, if desired).

In addition to the above copolymers, the polymeric regions for use in conjunction with the present invention also optionally contain supplemental polymers. Examples of supplemental polymers include a variety of homopolymers and copolymers (including alternating, random, statistical, gradient and block copolymers), which may be cyclic, linear or branched (e.g., the polymers may have star, comb or dendritic architecture), which may be natural or synthetic, and which may be thermoplastic or thermosetting. Specific polymers may be selected, for example, from one or more of the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides and polyether block amides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-olefin copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk), polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkyl oxide polymers and copolymers including polyethylene oxides (PEO); polyesters including polyethylene terephthalates and aliphatic polyesters such as polymers and copolymers of lactide (which includes lactic acid as well as d-,l-and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as copolymers of the above.

The supplemental polymers may be provided for various reasons. Supplemental polymers may be introduced, for example, to render the polymeric regions more hydrophilic, to modulate the release profile of a therapeutic agent, if any, among other reasons.

Further optional supplemental additives include particulate additives such as metallic and non-metallic inorganic particles. Such particles may be added, for example, to affect the mechanical or drug release (where a drug is present) properties of the polymeric regions of the invention. Suitable metallic particles include those formed, for example, from the following: substantially pure metals, such as silver, gold, platinum, palladium, iridium, osmium, rhodium, titanium, tungsten, and ruthenium, as well as metal alloys such as cobalt-chromium alloys, nickel-titanium alloys (e.g., nitinol), iron-chromium alloys (e.g., stainless steels, which contain at least 50% iron and at least 11.5% chromium), cobalt-chromium-iron alloys (e.g., elgiloy alloys), and nickel-chromium alloys (e.g., inconel alloys), among others. Suitable non-metallic particles include those formed, for example, from the following: calcium phosphate ceramics (e.g., hydroxyapatite); calcium-phosphate glasses, sometimes referred to as glass ceramics (e.g., bioglass); metal oxides, including non-transition metal oxides (e.g., oxides of metals from groups 13, 14 and 15 of the periodic table, including, for example, aluminum oxide) and transition metal oxides (e.g., oxides of metals from groups 3, 4, 5, 6, 7, 8, 9, 10, 11 and 12 of the periodic table, including, for example, oxides of titanium, zirconium, hafnium, tantalum, molybdenum, tungsten, rhenium, iridium, and so forth); carbon based materials such as pure and doped carbon (e.g., fullerenes, carbon nanofibers, single-wall, so-called "few-wall" and multi-wall carbon nanotubes), silicon carbides and carbon nitrides; silica; synthetic or natural silicates including aluminum silicate, monomeric silicates such as polyhedral oligomeric silsequioxanes (POSS), including various functionalized POSS and polymerized POSS, and phyllosilicates including clays and micas (which may optionally be intercalated and/or exfoliated) such as montmorillonite, hectorite, hydrotalcite, vermiculite and laponite.

Still further optional supplemental additives include plasticizers and other low molecular weight species.

As noted above, the medical devices of the present invention also optionally contain one or more therapeutic agents. "Therapeutic agents," "drugs," "pharmaceutically active agents," "pharmaceutically active materials," and other related terms may be used interchangeably herein. These terms include genetic therapeutic agents, non-genetic therapeutic agents and cells.

Exemplary non-genetic therapeutic agents for use in conjunction with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/ antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.).

Specific examples of non-genetic therapeutic agents include paclitaxel, (including particulate forms thereof, for instance, protein-bound paclitaxel particles such as albumin-bound paclitaxel nanoparticles, e.g., ABRAXANE), sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well a derivatives of the forgoing, among others.

Exemplary genetic therapeutic agents for use in conjunction with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor $\alpha$ and $\beta$, platelet-derived endothelial growth factor, platelet-derived growth factor, tumor necrosis factor $\alpha$, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in conjunction with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E-and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Further additional therapeutic agents useful for the practice of the present invention are also disclosed in U.S. Pat. No. 5,733,925 assigned to NeoRx Corporation, the entire disclosure of which is incorporated by reference.

Where a therapeutic agent is included, a wide range of therapeutic agent loadings can be used in conjunction with the medical devices of the present invention, with the therapeutically effective amount being readily determined by those of ordinary skill in the art and ultimately depending, for example, upon the condition to be treated, the age, sex and condition of the patient, the nature of the therapeutic agent, the nature of the polymeric region(s), and the nature of the medical device, among other factors.

Numerous techniques are available for forming polymeric regions in accordance with the present invention.

For example, in some embodiments, thermoplastic processing techniques are used to form the polymeric regions of the present invention. Using these techniques, polymeric regions can be formed by first providing a melt that contains the polymer(s) that form the polymeric region, along with any other optional additives, if desired, and subsequently cooling the melt. Examples of thermoplastic techniques include compression molding, injection molding, blow molding, spinning, vacuum forming and calendaring, as well as extrusion into sheets, fibers, rods, tubes and other cross-sectional profiles of various lengths. Using these and other thermoplastic processing techniques, a variety of polymeric regions can be formed.

In other embodiments, solvent-based techniques are used to form the polymeric regions of the present invention. Using these techniques, polymeric regions can be formed by first providing a solution that contains the polymer(s) that form the polymeric region, along with any other optional additives, if desired, and subsequently removing the solvent. The solvent that is ultimately selected will contain one or more solvent species, which are generally selected based on their ability to dissolve the polymer(s) and optional additives that make up the polymeric region, as well as other factors, including drying rate, surface tension, etc. Examples of solvent-based techniques include solvent casting techniques, spin coating techniques, web coating techniques, solvent spraying techniques, dipping techniques, techniques involving coating via mechanical suspension including air suspension, ink jet techniques, electrostatic techniques, and combinations of these processes, among others.

In some embodiments of the invention, a polymer containing solution (where solvent-based processing is employed) or polymer melt (where thermoplastic processing is employed) is applied to a substrate to form a polymeric region. For example, the substrate can correspond to all or a portion of an implantable or insertable medical device to which a polymeric region is applied. In these embodiments, the polymer may be applied over an adhesive promoter such as a silane, an inert hydrocarbon such as parylene, or a plasma treatment. The substrate can also be, for example, a template, such as a mold, from which the polymeric region is removed after solidification. In other embodiments, for example, fiber spinning, extrusion and co-extrusion techniques, one or more polymeric regions are formed without the aid of a substrate. In a more specific example, an entire stent body is extruded. In another, a polymeric layer is co-extruded along with an underlying stent body. In another, a polymeric layer is provided on an underlying step body by spraying or extruding a coating layer onto a pre-existing stent body. In yet another more specific example, a stent is cast in a mold.

If it is desired to provide one or more therapeutic agents (and/or any other optional additives) within the polymeric region, so long as these agents are stable under processing conditions, then they may be provided within the polymer containing solution or polymer melt and co-processed along with the polymer(s).

Alternatively, therapeutic and/or other optional additives may be introduced subsequent to the formation of the polymeric region in some embodiments. For instance, in some embodiments, the therapeutic and/or other optional additives are dissolved or dispersed within a solvent, and the resulting solution contacted (e.g., using one or more of the application techniques described above, such as dipping, spraying, etc.) with a previously formed polymeric region.

As noted above, barrier regions are provided over therapeutic-agent-containing regions in some embodiments of the invention. In these embodiments, a polymeric barrier region can be formed over a therapeutic-agent-containing region, for example, using one of the solvent based or thermoplastic techniques described above. Alternatively, a previously formed polymeric region can be adhered over a therapeutic agent containing region.

EXAMPLE 1

Synthesis of Poly(t-butyl vinyl ether-b-isobutyl vinyl ether-b-t-butyl vinyl ether)

In an exemplary procedure, polymerization is carried out in hexane/methyl chloride (Hex/CH$_3$Cl, 60/60, v/v) at −80° C. using the following species in the following concentrations: tert-butyl-dicumylchloride [tBuDiCumCl]=0.001 M, 2,6-di-tert-butylpyridine [DTBP]=0.004 M, [TiCl$_4$]=0.036 M, ditolyl ethylene [DTE]=0.004 M. Into a 75 mL test tube immersed in heptane at −80° C. are added 10.55 mL of Hex at room temperature, 6.21 mL of CH$_3$Cl at −80° C., 0.89 mL of DTBP stock solution in Hex at −80° C. (0.089 M), 1 mL of tBuDiCumCl stock solution in MeCl at −80° C. (0.02 M), and 1 mL of TiCl$_4$ stock solution in Hex/CH$_3$Cl (60/40, v/v) at −80° C. (0.72 M). About 5 min later, 1 mL of DTE stock solution in Hex/CH$_3$Cl (60/40, v/v) at −80° C. (0.08 M) is added. After 1 h, 2.65 mL of Ti[OCH(CH$_3$)$_2$]$_4$, also referred to herein as Ti(OIp)$_4$, stock solution in Hex/CH$_3$Cl (60/40, v/v) at −80° C. (0.271 M) is charged into the test tube. After ~2 min, 1.6 mL of isobutyl vinyl ether (IBVE) at room temperature is added. After 1 hour of polymerization, 1 mL of the reaction mixture is taken from the test tube and quenched with 2 mL of prechilled methanol for molecular weight measurement of the PIBVE middle segment ($M_n$=65.8 kg/mol; $M_w/M_n$=1.14). It is followed immediately by adding 1.06 mL Ti(OIp)$_4$ stock solution into the test tube. After ~2 min, 0.5 mL of t-butyl vinyl ether (tBVE) at room temperature is added. After 1 h, 2 mL of prechilled methanol is charged into the test tube to quench the reaction. After purification and drying in vacuo, the triblock copolymer weighs 1.31 g (Overall monomer conversion: 81%; $M_n$=81.3 kg/mol; $M_w/M_n$=1.19).

EXAMPLE 2

Synthesis of Poly(cyclohexyl vinyl ether-b-isobutyl vinyl ether-b-cyclohexyl vinyl ether)

In an exemplary procedure, polymerization is carried out in Hex/CH$_3$Cl (60/60, v/v) at −80° C. using the following concentrations: [tBuDiCumCl]=0.001 M, [DTBP]=0.004 M, [TiCl$_4$]=0.036 M, [DTE]=0.004 M. Into a 75 mL test tube immersed in heptane at −80° C. are added 10.55 mL of Hex at room temperature, 6.21 mL of CH$_3$Cl at −80° C., 0.89 mL of DTBP stock solution in Hex at −80° C. (0.089 M), 1 mL of tBuDiCumCl stock solution in MeCl at −80° C. (0.02 M), and 1 mL of TiCl$_4$ stock solution in Hex/CH$_3$Cl (60/40, v/v) at −80° C. (0.72 M). About 5 min later, 1 mL of DTE stock solution in Hex/CH$_3$Cl (60/40, v/v) at −80° C. (0.08 M) is added. After 1 h, 2.65 mL of Ti(OIp)$_4$ stock solution in Hex/CH$_3$Cl (60/40, v/v) at −80° C. (0.271 M) is charged into the test tube. After ~2 min, 1.6 mL of IBVE at room temperature is added. After 1 hour of polymerization, 1 mL of the reaction mixture is taken from the test tube and quenched with 2 mL of prechilled methanol for molecular weight measurement of the PIBVE middle segment ($M_n$=61.7 kg/mol; $M_w/M_n$=1.16). It is followed immediately by adding 1.31 mL of Ti(OIp)$_4$ stock solution into the test tube. After ~2 min, 0.5 mL of cyclohexyl vinyl ether (CHVE) at room temperature is added. After 1 h, 2 mL of prechilled methanol is charged into the test tube to quench the reaction. After purification and drying in vacuo, the triblock copolymer weighs 1.49 g (Overall monomer conversion: 89%; $M_n$=77.6 kg/mol; $M_w/M_n$=1.17).

EXAMPLE 3

Paclitaxel Elution from Coated Stents

Stent coating solutions are provided that contain 25 wt % THF and 74 wt % toluene, 0.25 wt % paclitaxel and 0.75 wt % polymer. All solutions are prepared by mixing the polymer, solvent and paclitaxel, thoroughly mixing (e.g., overnight), and filtering. The following polymer solutions are made: (1) a solution. containing 0.25 wt % paclitaxel and 0.75 wt % poly(styrene-b-isobutylene-b-styrene triblock copolymer (SIBS), prepared as described in United States Patent Application 20020107330 and U.S. Pat. No. 6,545,097 entitled "Drug delivery compositions and medical devices containing block copolymer"; (2) a solution containing 0.25 wt % paclitaxel and 0.75 wt % poly(tert-butyl vinyl ether-b-isobutyl vinyl ether-b-tert-butyl vinyl ether) prepared as described above; (3) a solution containing 0.25 wt % paclitaxel and 0.75 wt % poly(cyclohexyl vinyl ether-b-isobutyl vinyl ether-b-cyclohexyl vinyl ether) triblock copolymer prepared as described above.

Each solution is then coated by spray coating as described, for example, in U.S. Patent App. Pub. No. 2003/0236514 to Schwarz. At least five stents are formed in this manner for each of the solutions.

Paclitaxel release is then measured as a function of time in PBS containing 0.5 wt % Tween® 20 (polyoxyethylene(20) sorbitan monolaurate) available from Sigma-Aldrich. The results, presented as the percentage of paclitaxel in the stent that is released as a function of time, are graphically illustrated in FIG. 1.

Figure 2:
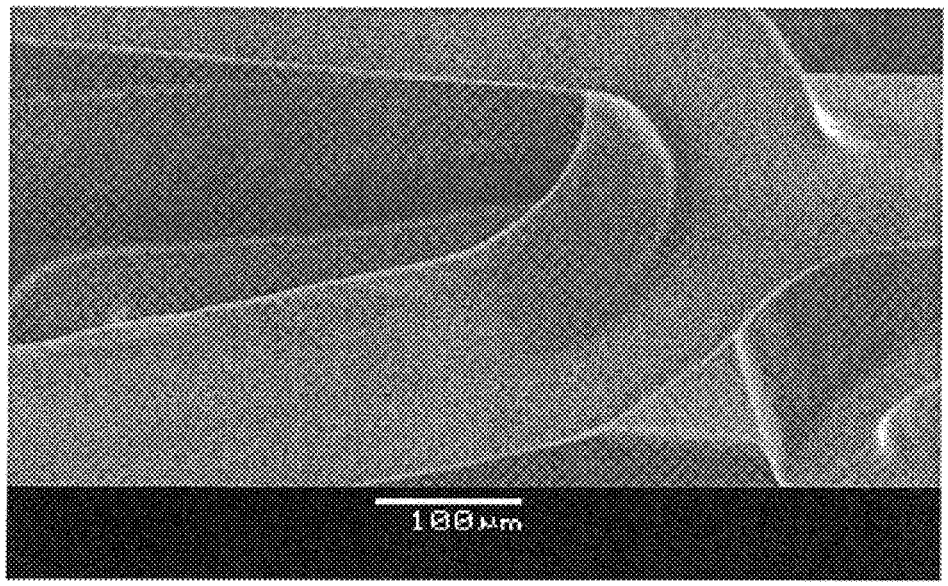
FIGS. 2 and 3 are each SEM micrographs of a stent having a polymer coating containing paclitaxel and poly(t-butyl vinyl ether-b-isobutyl vinyl ether-b-t-butyl vinyl ether), in accordance with an embodiment of the invention.
Figure 3:
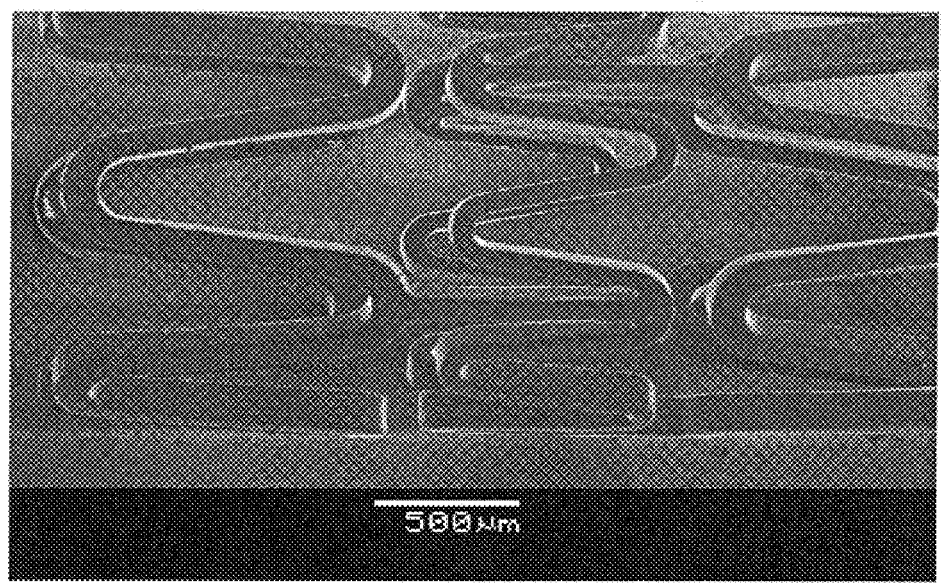
Figure 4:
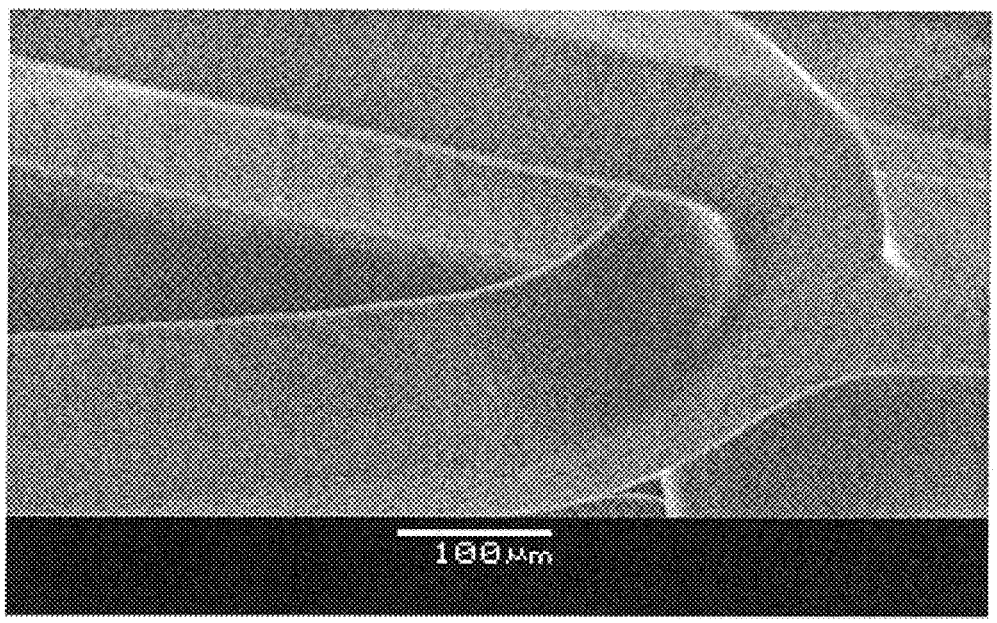
FIGS. 4 and 5 are each SEM micrographs of a stent having a polymer coating containing paclitaxel and poly(cyclohexyl vinyl ether-b-isobutyl vinyl ether-b-cyclohexyl vinyl ether), in accordance with an embodiment of the invention.
Figure 5:
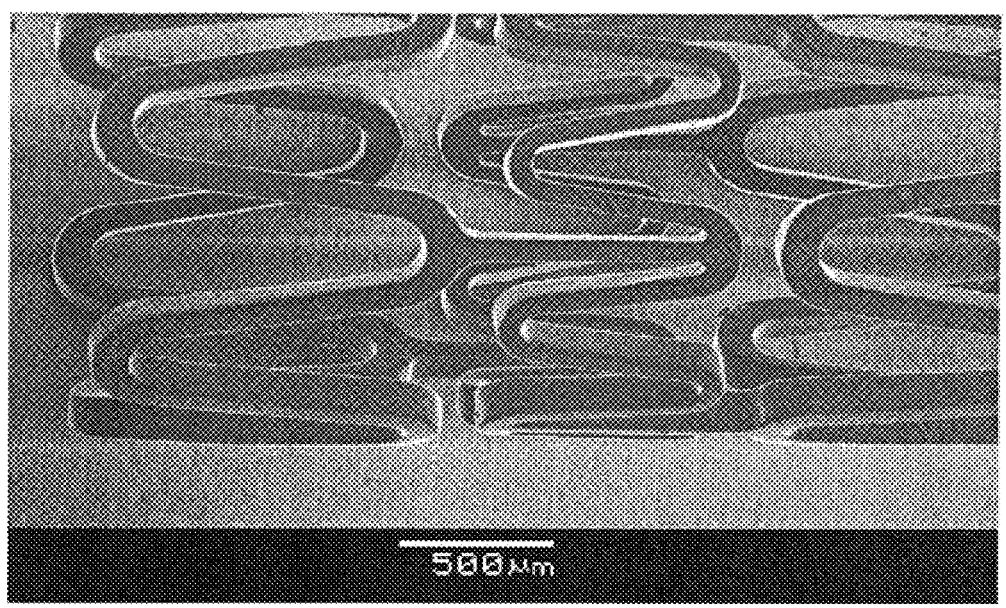

SEM micrographs for stents produced using solution (2) above are found in FIGS. 2 and 3. SEM micrographs for stents produced using solution (3) above are found in FIGS. 4 and 5. These micrographs demonstrate that the coating was durable and did not display the usual failure modes for inadequate stent coatings such as cracking or delamination.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising a polymeric region, said polymeric region comprising a block copolymer that comprises (a) a high $T_g$ polymer block comprising a high $T_g$ vinyl ether monomer and (b) a low $T_g$ polymer block comprising a low $T_g$ vinyl ether monomer, said medical device being adapted for implantation or insertion into a subject's body.

2. The medical device of claim 1, wherein said copolymer comprises plurality of high $T_g$ polymer blocks.

3. The medical device of claim 1, wherein said high $T_g$ polymer block comprises plurality of differing high $T_g$ vinyl ether monomers.

4. The medical device of claim 1, wherein said high $T_g$ polymer block comprises a high $T_g$ alkyl vinyl ether monomer comprising from 1 to 20 carbon atoms.

5. The medical device of claim 1, wherein said high $T_g$ polymer block comprises a high $T_g$ vinyl ether monomer selected from tert-butyl vinyl ether and cyclohexyl vinyl ether.

6. The medical device of claim 1, wherein said copolymer comprises plurality of low $T_g$ polymer blocks.

7. The medical device of claim 1, wherein said low $T_g$ polymer block comprises plurality of differing low $T_g$ vinyl ether monomers.

8. The medical device of claim 1, wherein said low $T_g$ polymer block comprises a low $T_g$ alkyl vinyl ether monomer comprising from 1 to 20 carbon atoms.

9. The medical device of claim 1, wherein said low $T_g$ polymer block comprises a low $T_g$ vinyl ether monomer selected from methyl vinyl ether, ethyl vinyl ether, propyl vinyl ether, butyl vinyl ether, isobutyl vinyl ether, 2-ethylhexyl vinyl ether, dodecyl vinyl ether, and combinations thereof.

10. The medical device of claim 1, wherein said block copolymer is a branched copolymer.

11. The medical device of claim 1, wherein said block copolymer is a linear copolymer.

12. The medical device of claim 1, wherein said block copolymer comprises a central low $T_g$ polymer block and two high $T_g$ polymer end blocks.

13. The medical device of claim 1, wherein said block copolymer comprises a central poly(isobutyl vinyl ether) block and two poly(cyclohexyl vinyl ether) end blocks.

14. The medical device of claim 1, wherein said block copolymer comprises a central poly(isobutyl vinyl ether) block and two poly(tert-butyl vinyl ether) end blocks.

15. The medical device of claim 1, wherein said polymeric region comprises at least 75 wt % of said block copolymer.

16. The medical device of claim 1, wherein said medical device further comprises a therapeutic agent.

17. The medical device of claim 16, wherein said therapeutic agent is disposed beneath said polymeric region.

18. The medical device of claim 16, wherein said therapeutic agent is disposed within said polymeric region.

19. The medical device of claim 18, wherein a baffler layer is disposed over said polymeric region.

20. The medical device of claim 16, wherein said therapeutic agent is selected from anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, agents that interfere with endogenous vasoactive mechanisms, and combinations thereof.

21. The medical device of claim 1, wherein said polymeric region further comprises a supplemental polymer in addition to said block copolymer.

22. The medical device of claim 1, wherein said polymeric region further comprises a plasticizer.

23. The medical device of claim 1, wherein said polymeric region further comprises inorganic particles.

24. The medical device of claim 1, wherein said polymeric region is disposed over a substrate.

25. The medical device of claim 24, wherein an adhesive promoter is disposed between said polymeric region and said substrate.

26. The medical device of claim 1, wherein said medical device is selected from a guide wire, a balloon, a vena cava filter, a catheter, a stent, a stent graft, a vascular graft, a cerebral aneurysm filler coil, a myocardial plug, a heart valve, a vascular valve, and a tissue engineering scaffold.

27. The medical device of claim 1 wherein the block copolymers are selected from the group consisting of:
(a) block copolymers having alternating blocks of the type $(HL)_m$, $L(HL)_m$ and $H(LH)_m$ where L is a low $T_g$ polymer block, H is a high $T_g$ polymer block and m is a positive whole number of 1 or more; and
(b) block copolymers having multi-arm geometries, which block copolymers are selected from $X(LH)_n$, and $X(HL)_n$, where n is a positive whole number of 2 or more and X is a hub species.

* * * * *